(12) United States Patent
Wojtach et al.

(10) Patent No.: US 10,982,773 B2
(45) Date of Patent: Apr. 20, 2021

(54) GAS CONCENTRATOR APPARATUS AND METHOD OF USE THEREOF

(71) Applicants: Peter Wojtach, Port Jefferson Station, NY (US); Greg Marler, Rockford, IL (US)

(72) Inventors: Peter Wojtach, Port Jefferson Station, NY (US); Greg Marler, Rockford, IL (US)

(73) Assignee: Peter Wojtach, Port Jefferson Station, NY (US)

( * ) Notice: Subject to any disclaimer, the term of this patent is extended or adjusted under 35 U.S.C. 154(b) by 440 days.

(21) Appl. No.: 15/723,930

(22) Filed: Oct. 3, 2017

(65) Prior Publication Data

US 2018/0094730 A1 Apr. 5, 2018

Related U.S. Application Data

(63) Continuation-in-part of application No. 15/283,429, filed on Oct. 2, 2016, now abandoned.

(51) Int. Cl.
*A61M 16/20* (2006.01)
*F16K 1/32* (2006.01)
(Continued)

(52) U.S. Cl.
CPC ........... *F16K 1/32* (2013.01); *A61M 16/0816* (2013.01); *A61M 16/101* (2014.02); *A61M 16/20* (2013.01)

(58) Field of Classification Search
CPC .............. A61M 11/02; A61M 16/0808; A61M 16/0833; A61M 16/208; A61M 2039/1033; A61M 39/10; A61M 39/26; A62B 7/00; A62B 9/00; A62B 9/02; B25C 1/008; B25F 5/00; F16K 1/307; F16K 17/04; F16L 37/05; F16L 37/113; F16L 37/32; F16L 37/40; F17C 13/04; F17C 2201/0109; F17C 2205/0332; F17C 2205/0338; F17C 2205/0382; F17C 2205/0394; F17C 2221/011; F17C 2223/0123; F17C 2250/043; F17C 2250/0626; F17C 2270/025; Y10S 128/912; Y10S 251/90;
(Continued)

(56) References Cited

U.S. PATENT DOCUMENTS 3,486,730 A * 12/1969 Potash .................... F16L 37/40
251/149.7
3,771,762 A * 11/1973 Mayernik ............... F16L 37/02
251/148
(Continued)

*Primary Examiner* — Annette Dixon
(74) *Attorney, Agent, or Firm* — Leason Ellis LLP

(57) ABSTRACT

An apparatus and method for automatically controlling the flow of oxygen from a gas source is provided and includes the step of installing a gas concentrator device on an outlet port associated with the gas source. The gas concentrator device is configured to sealingly mate with a conduit connector for delivering a gas from the gas source to a conduit that is associated with the conduit connector. The method also includes the step of automatically providing gas flow from the gas source to the conduit by sealingly coupling the conduit connector to the gas concentrator device and whereupon removal of the conduit connector from the gas concentrator device causes the gas flow to automatically cease.

26 Claims, 17 Drawing Sheets

(51) Int. Cl.
*A61M 16/10* (2006.01)
*A61M 16/08* (2006.01)

(58) Field of Classification Search
CPC ......... Y10T 137/2642; Y10T 137/6116; Y10T 137/7791; Y10T 137/7869; Y10T 137/7931; Y10T 137/87957; Y10T 137/88046
See application file for complete search history.

(56) References Cited

U.S. PATENT DOCUMENTS

| | | | | |
|---|---|---|---|---|
| 4,033,378 | A | * | 7/1977 | Pauliukonis ............ F16K 1/307 137/614.19 |
| 4,714,077 | A | * | 12/1987 | Lambert .................. A62B 9/00 128/202.27 |
| 4,834,131 | A | * | 5/1989 | Austin .................... B25C 1/008 137/115.26 |
| 4,951,661 | A | * | 8/1990 | Sladek .............. A61M 16/0808 128/202.27 |
| 5,009,252 | A | * | 4/1991 | Faughn ................ F16L 37/113 137/614.04 |
| 5,241,955 | A | | 9/1993 | Dearman et al. |
| RE34,426 | E | * | 11/1993 | Weaver .................. F16L 37/12 137/614 |
| 5,619,988 | A | * | 4/1997 | Mattila .................... A62B 9/02 128/205.24 |
| 6,116,242 | A | | 9/2000 | Frye et al. |
| 7,708,016 | B2 | | 5/2010 | Zaiser et al. |
| 8,276,584 | B2 | | 10/2012 | Tatarek |

* cited by examiner

GAS CONCENTRATOR APPARATUS AND METHOD OF USE THEREOF

CROSS-REFERENCE TO RELATED APPLICATION

The present application is a continuation-in-part application of U.S. patent application Ser. No. 15/283,429, filed Oct. 2, 2016, which is hereby incorporated by reference in its entirety.

TECHNICAL FIELD

The present invention disclosed herein generally relates to medical ventilator systems, and more particularly, relates to a gas concentrator apparatus for supplying a gas, for example, oxygen, to a patient.

BACKGROUND

Individuals undergoing treatment at hospitals sometimes have difficulty breathing based on the nature of the ailment. Moreover, some patients may have a failed lung to an accident. Such disabilities or conditions require external assistance for inspiration and expiration of breathing gases. Conventionally, medical ventilator systems assist individuals or patients in inspiring oxygen and expiring carbon dioxide. Typically, oxygen is supplied from oxygen tanks to the ventilator via flow meters. Flow meters enable the practitioner or nurse to regulate the proportion of the oxygen supplied to the patient. If there is a decrease in the percentage of oxygen supplies to the patient, the flow meter is adjusted to supply more oxygen. Alternatively, if the supplied air contains high proportion of oxygen, the supply from the oxygen tank is stopped. Sometimes, while using the flow meters, operators tend to leave the flow meters open even when the requirement has been met. This forces oxygen to flow out at high velocity and empty the oxygen cylinders resulting in waste. Moreover, when transporting patients who are supplied oxygen by the oxygen tanks, negligence in the closing of the flow meters leads to unnecessary waste or emptying of the oxygen tanks. Hence, there is a long felt but unresolved need for an apparatus, which prevents the loss of oxygen when supply of oxygen via flow meters is left open due to operator negligence.

SUMMARY

According to one embodiment, a gas connector device includes a valve body having a first end configured to sealingly mate with an outlet port associated with a gas source and a second end configured to sealingly mate with a conduit for delivering gas from the gas source. The gas connector device further includes a valve mechanism that is at least partially contained within the valve body and is configured to automatically move between an open position in which the gas is permitted to flow from the gas source through the valve body into the conduit and a closed position in which gas is prevented from flowing from the gas source through the valve body into the conduit. The valve mechanism is configured such that connecting the conduit to the valve body automatically opens the valve mechanism and removal of the conduit from the valve body automatically closes the valve mechanism.

In another aspect, a method for automatically controlling the flow of oxygen from a gas source is provided and includes the step of installing a gas concentrator device on an outlet port associated with the gas source. The gas concentrator device is configured to sealingly mate with a conduit connector for delivering a gas from the gas source to a conduit that is associated with the conduit connector. The method also includes the step of automatically providing gas flow from the gas source to the conduit by sealingly coupling the conduit connector to the gas concentrator device and whereupon removal of the conduit connector from the gas concentrator device causes the gas flow to automatically cease.

The gas concentrator device has a valve mechanism that is configured to automatically open when the conduit connector is sealingly coupled to the gas concentrator device and is configured to automatically close when the conduit connector is removed from the gas concentrator device.

By configuring the gas concentrator device to automatically shut off when the conduit connector is removed therefrom, increased safety is realized since this action prevents the unintended release of the gas into the room.

BRIEF DESCRIPTION OF THE DRAWING FIGURES

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF CERTAIN EMBODIMENTS

Figure 1:
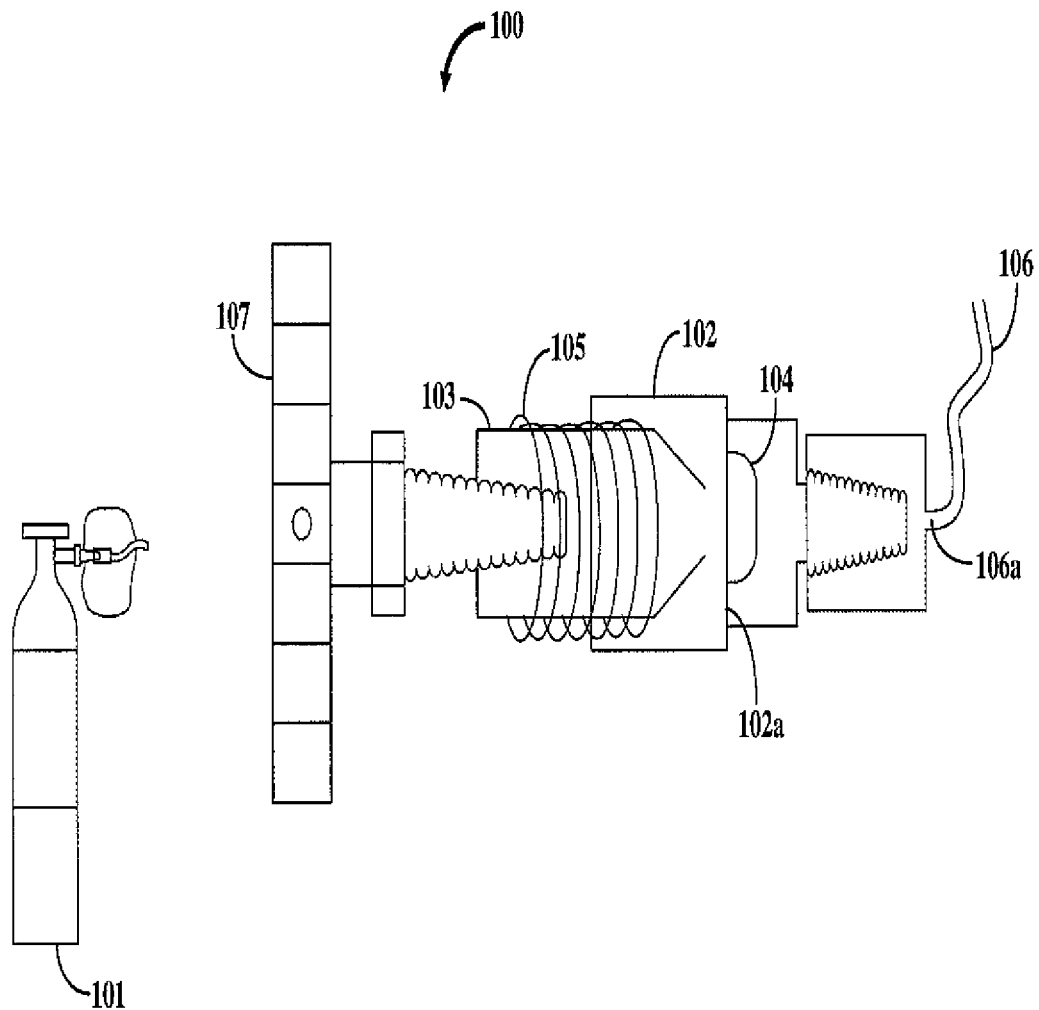
FIG. 1 is an exemplary schematic diagram of a gas concentrator device (apparatus) according to a first embodiment.

FIG. 1 is a schematic diagram of an exemplary gas concentrator device (apparatus) 100. The gas concentrator apparatus 100, disclosed herein, comprises a gas source 101, a chamber 102, a piston 103, a membrane 104, a spring 105 and a gas supply tube 106. In an embodiment, the chamber 102 is in gaseous communication with a gas source 101 for receiving the gas from the gas source 101 which can be in the form of a gas storage tank. In an embodiment, the gas source 101 is, for example, an oxygen storage tank, etc. The gas source 101 is connected to the chamber 102 via a flow meter 107. The flow meter 107 regulates the flow of the gas from the gas source 101 to the chamber 102. The oxygen then flows through the entrance 106a of the gas supply tube 106 to a patient. In an embodiment, the chamber 102 comprises a piston 103 configured to move the chamber 102 in a forward direction or a reverse direction. The membrane 104 is positioned at an end 102a of the chamber 102 distal to the gas source 101.

In an embodiment, the membrane 104 is actuated by the spring 105 to seal an entrance 106a of the gas supply tube 106 for preventing leakage of the gas when the gas supply tube 106 is removed from the gas concentrator apparatus 100. The gas concentrator apparatus 100 is a spring-loaded device that prevents the flow of oxygen after the gas supply tube 106 is disconnected. The gas concentrator apparatus 100 stops the flow of oxygen and prevents the loss of oxygen from the open flow meter 107. This prevents leakage of oxygen and prolongs the life of the gas source 101. Moreover, the gas concentrator apparatus 100 helps reduce costs by reducing wastage of the oxygen supplied to the patient.

Figure 2:
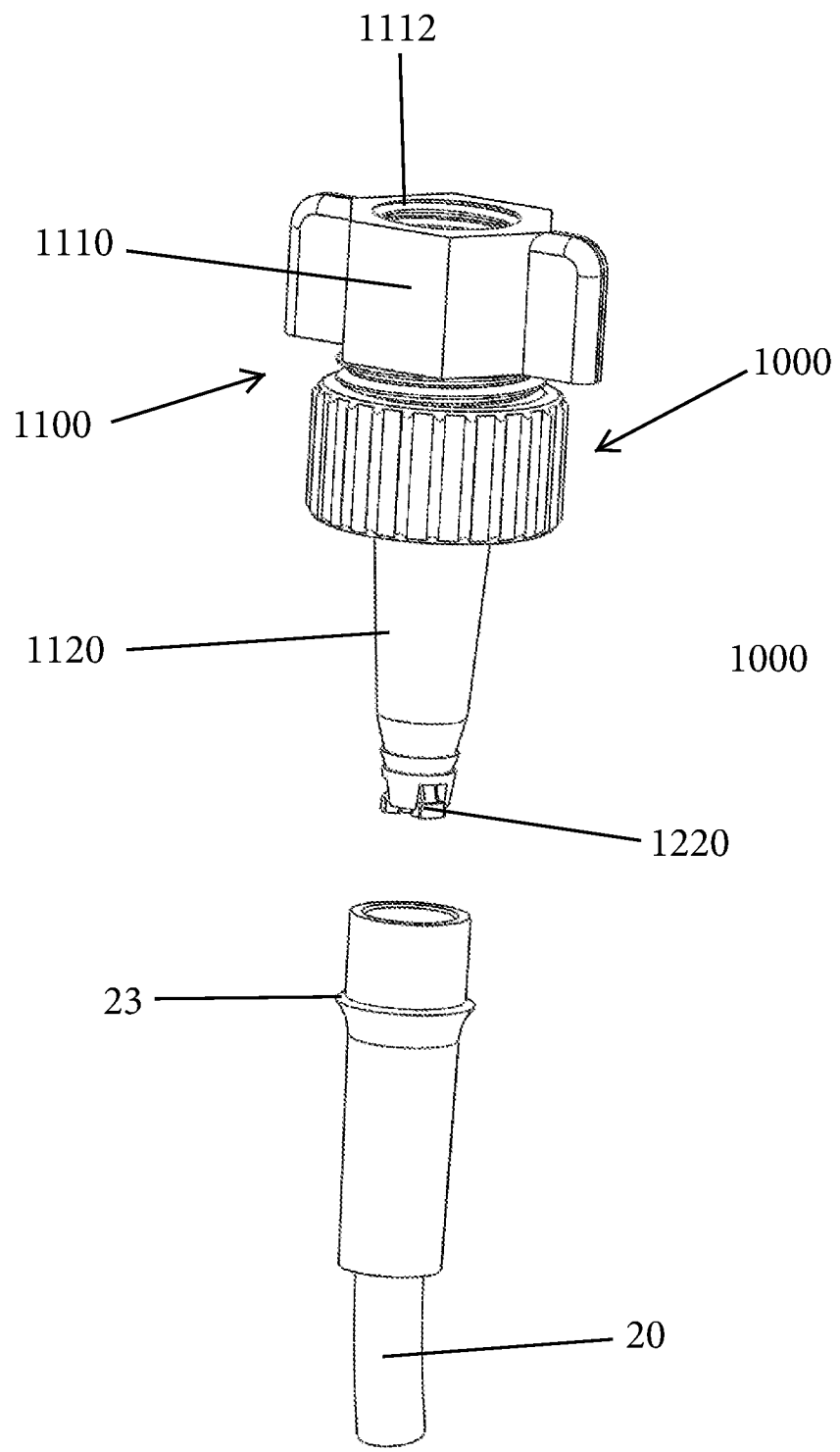
FIG. 2 is an exploded perspective view of a gas concentrator device or assembly according to a second embodiment.
Figure 3:
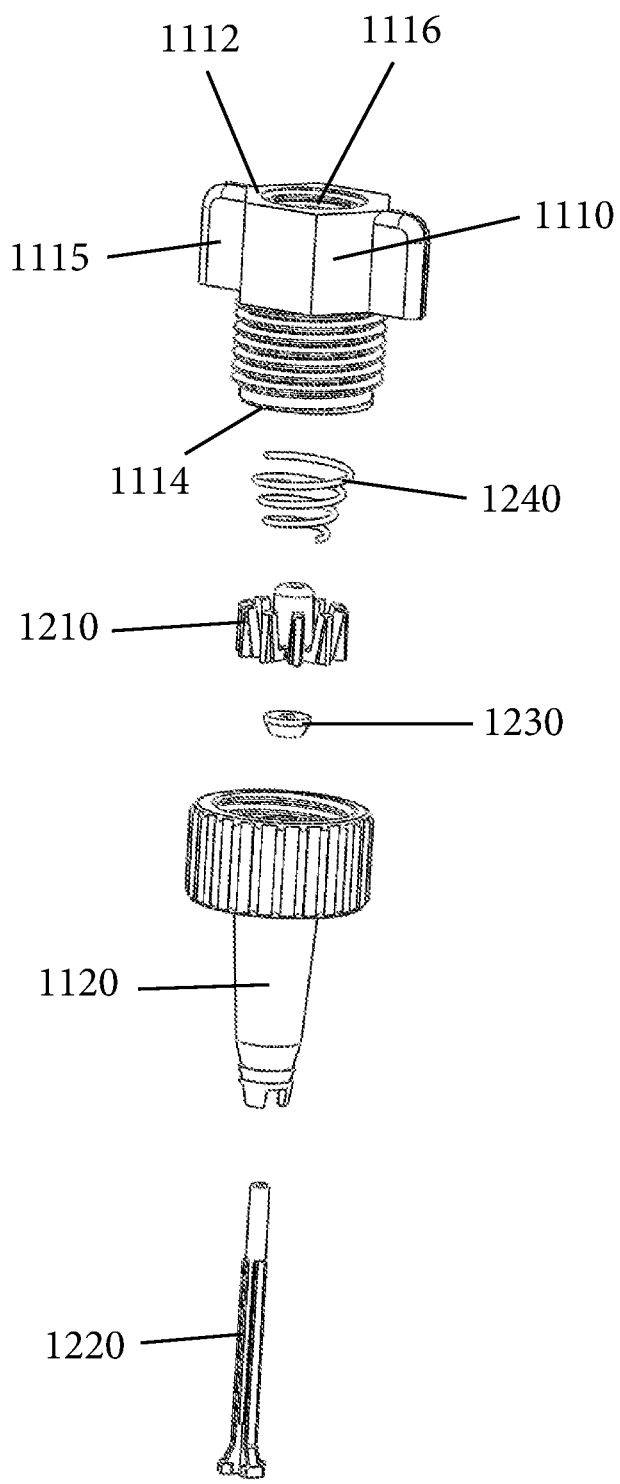
FIG. 3 is an exploded perspective view thereof.

FIGS. 2-12B illustrate a gas connector device 1000 that is similar to the gas concentrator apparatus 100. The gas connector device 1000 is formed of a number of parts (components). FIG. 2 shows the gas connector device 1000 in an assembled state, while FIG. 3 shows the gas connector device 1000 in an exploded view. Similar to the gas concentrator apparatus 100, the gas connector device 1000 is configured for being fluidly and sealingly coupled to a gas source 101 (FIG. 1) and also is configured for being fluidly and sealingly coupled to a conduit 20 (e.g., tubing) that is intended to deliver the gas from the gas source 101 to a remote device, such as a face mask, etc. For example, the gas source 101 can be an oxygen tank and the conduit 20 can be in the form of oxygen tubing. In particular, the gas source 101 can be in the form of an oxygen tank that has a flow meter, such as the flow meter 107 (FIG. 1). As is known, the flow meter is a device that meters the outflow of gas from the gas source 101 and typically includes a controller, such as a dial, that allows for adjustment of the metered amount (i.e., gas flow rate of the gas contained in the gas source 101). The flow meter includes an outlet port that protrudes outwardly from the flow meter and can be in the form of a barbed, angled structure that is configured to receive and be secured to a conduit, such as the conduit 20. The outlet port can have a frusto-conical shape and thus, when the conduit 20 has this shape, it generally has a Christmas tree shape.

FIG. 2 illustrates one exemplary conduit 20. The conduit 20 is a flexible tubing (e.g. plastic tubing) that can fit over a coupling structure, such as outlet port or a similar port structure such as the one incorporated into the device 1000 as described herein. The conduit 20 can include a conduit connector 23 at a distal end of the conduit 20. In one embodiment, the conduit connector 23 has a different stiffness relative to the conduit 20; however, the conduit connector 23 and conduit 20 are an integral structure. For example, the conduit connector 23 can be overmolded with the conduit 20 to form an integral structure. The conduit connector 23 thus is a hollow part with a central lumen. The central lumen can have a non-uniform diameter (width). For example, the central lumen can have a tapered opening.

The exploded perspective view of the device 1000 (FIG. 3) delineates the different parts of the device 1000. Generally, the device 1000 has a housing 1100 and a valve assembly 1200. The housing 1100 includes a first connector fitting 1110 and a second connector fitting 1120 that is configured to mate with and seal with the first connector fitting 1110. The first connector fitting 1110 has a first end 1112 and a second end 1114 and is hollow in that a central lumen extends therethrough from the first end 1112 to the second end 1114. The first end 1112 is configured to mate with the flow meter 12 and in particular, the outlet port 13. In one embodiment, the outlet port 13 can be in the form of a threaded fitting and in particular, the outlet port 13 can have outer threads. The first end 1112 of the first connector fitting 1110 has complementary inner (female) threads 1116 that threadingly mate with the outer (male) threads of the outlet port 13 for coupling the first connector fitting 1110 to the outlet port 13 in a sealed manner.

The first end 1112 of the first connector fitting 1110 can have external (tightening) tabs 1115 or other structures that assist in the user rotating the first connector fitting 1110 as the first connector fitting 1110 is being attached or detached from the outlet port 13. For example, the tabs 1115 can be longitudinal ribs that extend along a length of the first connector fitting 1110. As illustrated, an outer surface of a first end portion of the first connector fitting 1110 that terminates in the first end 1112 is shaped to allow for tightening or loosening of the first connector fitting 1110. For example, the outer surface can have one or more planer section (flats) against which a tool can be seated (e.g., hexagon). The tabs 1115 also define part of this outer surface. Thus, in one embodiment, opposing tabs 1115 are provided on each side of the hexagonal body of the fitting to assist in hand tightening the first connector fitting 1110 to the gas source 101.

The second end 1114 of the first connector fitting 1110 has outer (male) threads 1119. As shown, the second end portion that terminates in the second end 1114 can have a cylindrical shape with the outer threads 1119 being formed along the outer surface thereof. As shown, each of the first end portion and the second end portion can be essentially one half of the length of the first connector fitting 1110. The outer (male) threads 1119 are mated to complementary female threads of the second connector fitting 1120 as described below.

It will be understood that the inner (female) thread 1116 can also be configured as a male thread, quick disconnect mechanism or other configuration suitable for interface with the gas source 101.

Figure 11A:
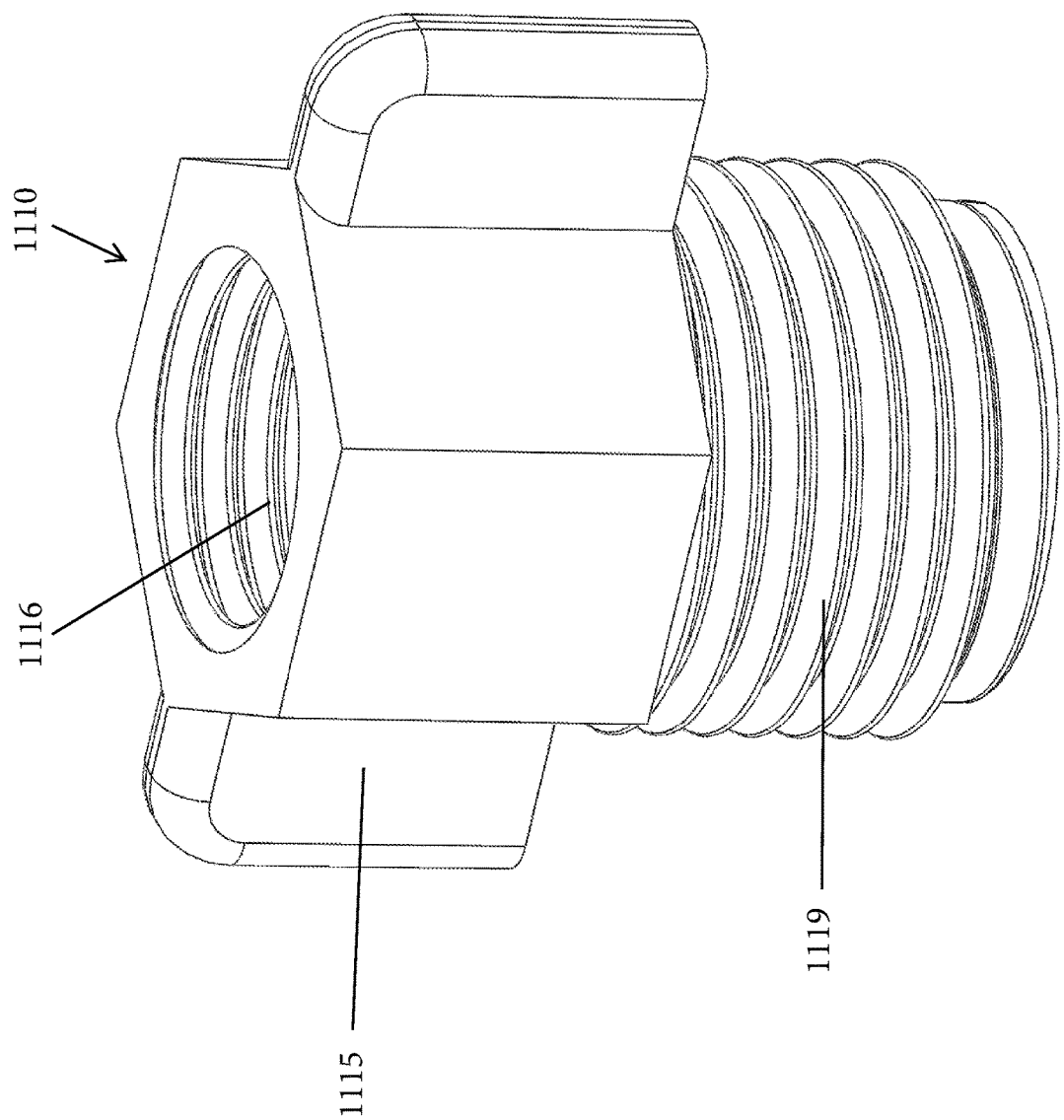
FIG. 11A is a perspective view of a first part (first fitting) of the gas concentrator device.
Figure 11B:
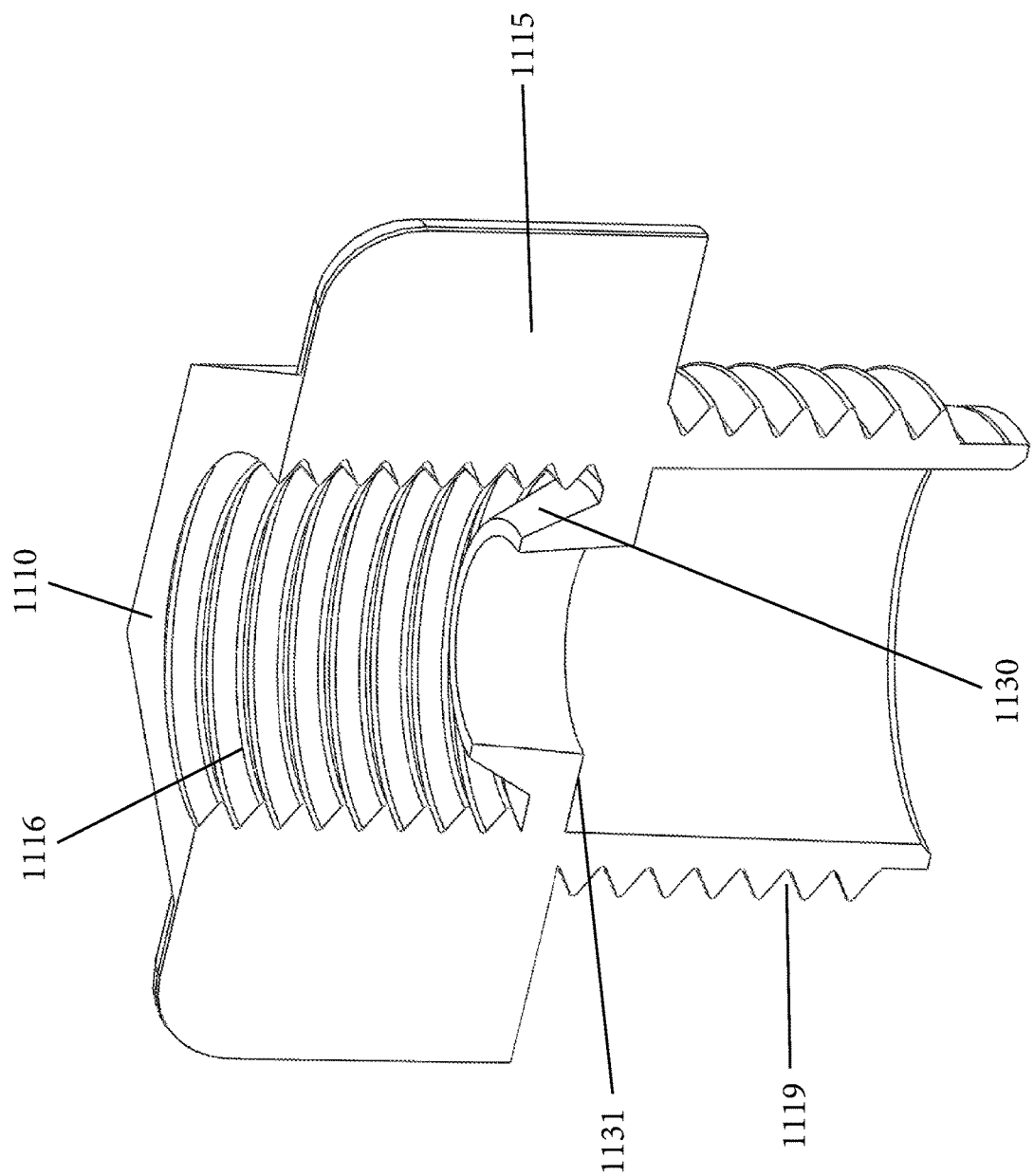
FIG. 11B is a cross-sectional perspective view thereof.

As shown in the cross-sectional view of FIG. 11B, the first connector fitting 1110 has an internal seat 1130 which is located below the inner threads 1116 and can therefore, be centrally located within the first connector fitting 1110. The internal seat 1130 can have a conical shape as shown that tapers inwardly toward the first end 1112 of the first connector fitting 1110. The internal seat 1130 is configured to provide a leak free connection to the outlet port 13 when the first connector fitting 1110 mates to the outlet port 13. The internal seat 1130 can be of varying design based on the geometry of the gas source.

Figure 12A:
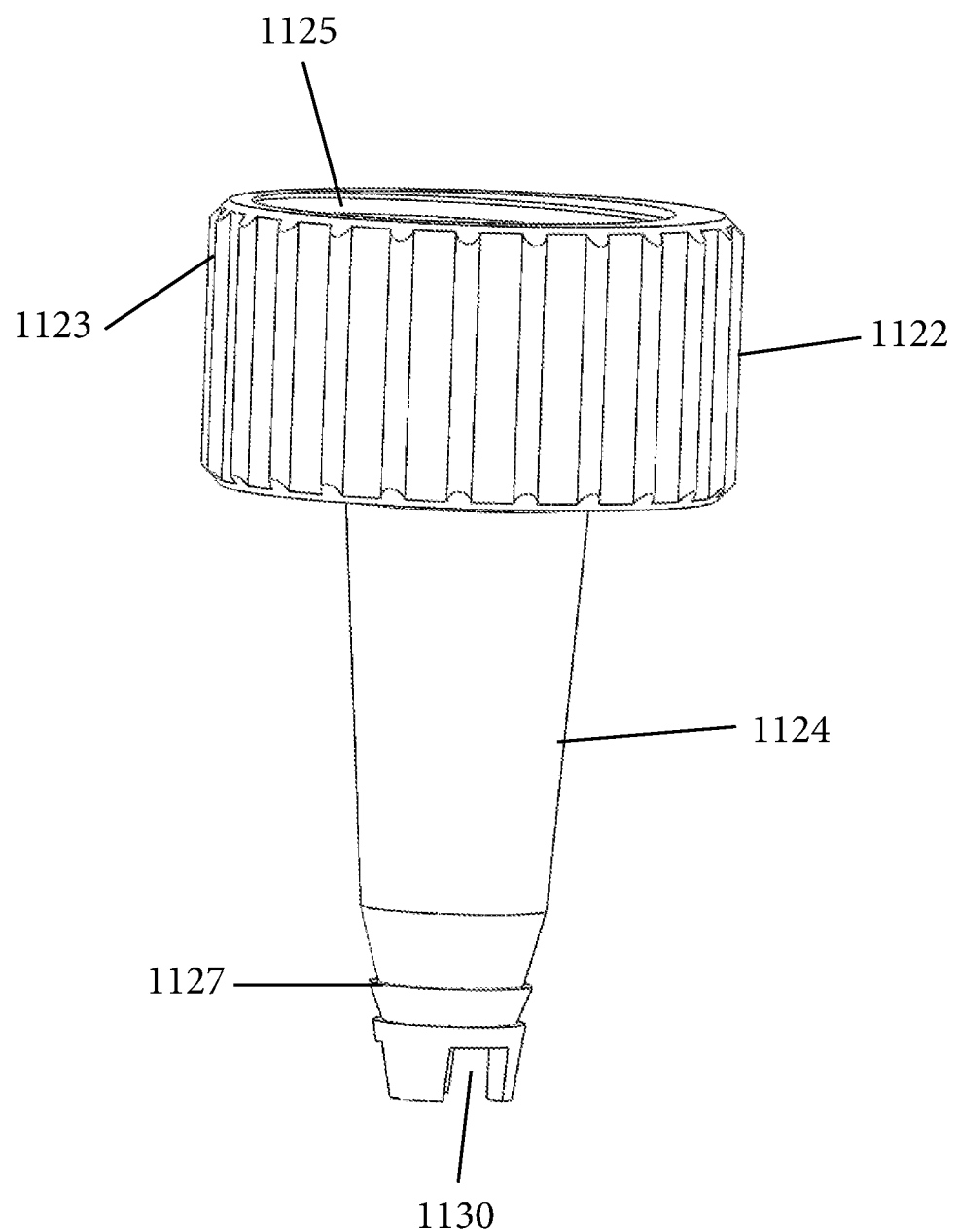
FIG. 12A is a perspective view of a second part (second fitting) of the gas concentrator device.
Figure 12B:
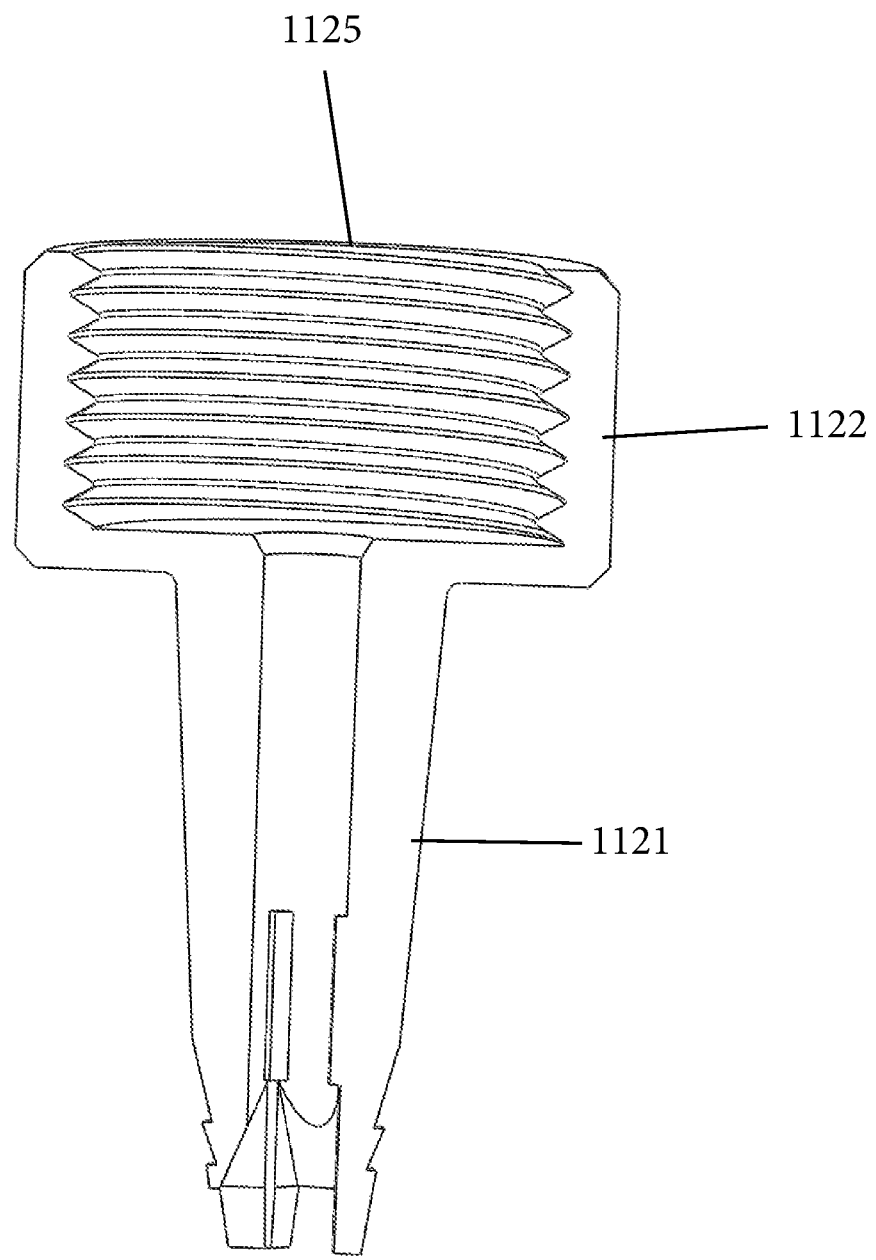
FIG. 12B is a cross-sectional perspective view thereof.

As shown in FIGS. 3, 12A, and 12B, the second connector fitting 1120 is a hollow body that has a first end portion 1122 and a second end portion 1124. The first end portion 1122 is a coupling portion that is configured to sealingly mate with the first connector fitting 1110. The first end portion 1122 can be an annular shaped structure with internal threads 1125 formed therein. The internal threads 1125 are configured to threadingly mate with the outer threads 1119 of the first connector fitting 1110, thereby resulting in connection between the first connector fitting 1110 and the second connector fitting 1120.

An outer surface of the first end portion 1122 can include tightening ribs 1123 that are formed therealong and extend longitudinally. The ribs 1123 assist in the user tightening the second connector fitting 1120 relative to the first connector fitting 1110.

The second end portion 1124 of the second connector fitting 1120 is also a hollow structure that has a frusto-conical shape and is open at the distal end thereof. A distal end of the second end portion 1124 includes a guide slot 1149. The guide slot 1149 can comprise a plurality of notches formed in the tapered second end portion 1124 at the distal end thereof. Each notch is thus in the form of a cutout. As described herein, each cutout receives complementary shaped parts that are discussed below. One or more barbs 1127 can be formed along the exterior (outer) surface of the second end portion 1124 to assist in providing a sealed connection between the second connector fitting 1120 and the conduit connector 23.

As shown in FIG. 12B, one or more ribs 1121 are provided radially about the center bore of the second connector fitting 1120 to aid in positioning the valve assembly 1200 as described in more detail below.

As shown in FIGS. 2, 4A, 4B, and 8-10, the valve assembly 1200 also is formed of a number of parts that are coupled to one another to form the valve assembly 1200. As shown in the figures, the valve assembly 1200 includes a valve poppet 1210, a valve stem 1220, and a spring 1240 that are coupled to one another to form the valve assembly 1200.

Figure 6:
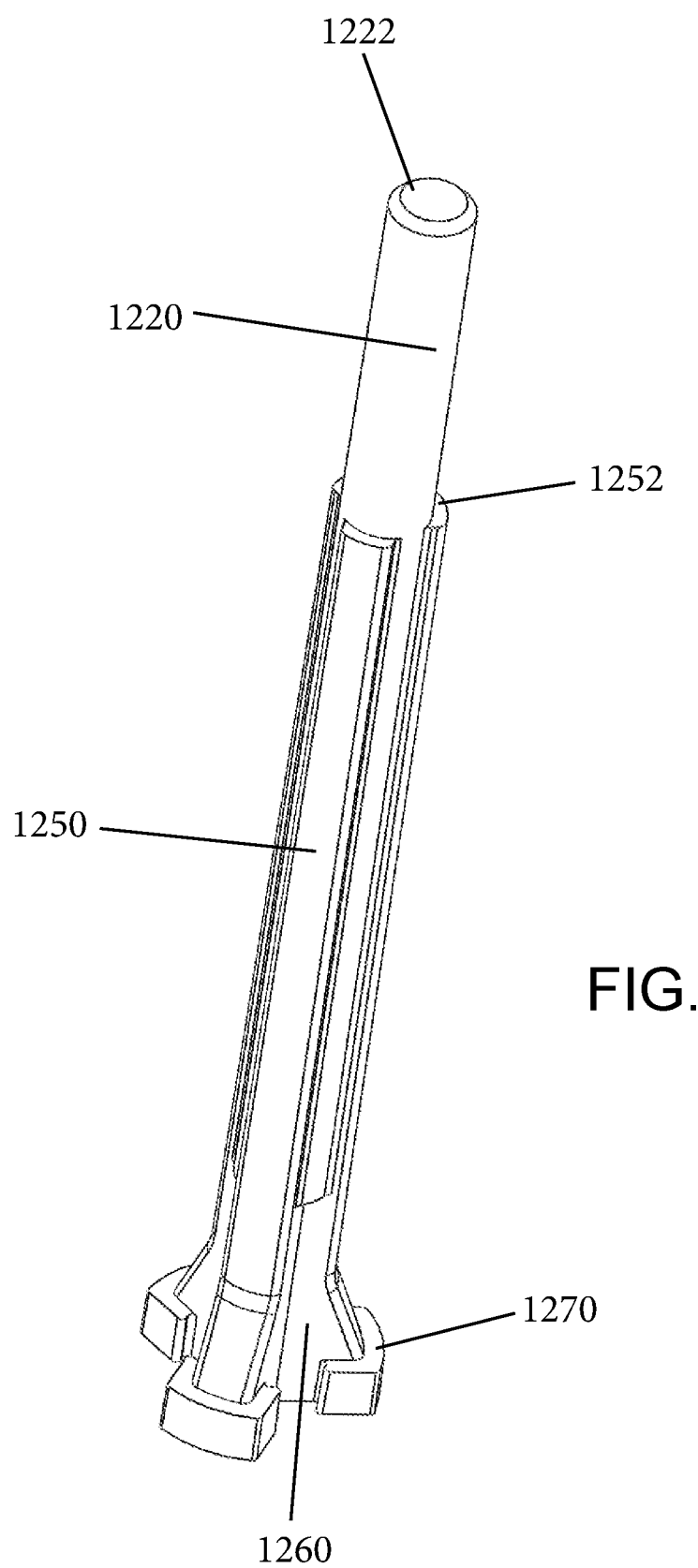
FIG. 6 is a perspective view of a valve stem of the valve assembly.

As shown in FIG. 6, the valve stem 1220 is an elongated structure that has a first end 1222 and an opposing second end 1224. The valve stem 1220 can have a cylindrical shape as shown and includes a plurality of longitudinal ribs 1250. The longitudinal ribs 1250 do not extend the entire length of the valve stem 1220. The longitudinal ribs 1250 provide strength to the valve stem 1220. At a proximal end of each rib 1250 is a proximal shoulder 1252 acting to locate the distal surface of a valve seat 1230. Each rib 1250 has a fin 1260 located at a distal end of the rib 1250. As shown, the fin 1260 can have a delta or triangular shape in that the fin 1260 flares radially outward from the valve stem 1220. The fin 1260 provides a robust structural foundation for a fin flange 1270. The fin flanges 1270 are the mechanical elements which directly contact the inside diameter of the conduit connector 23 upon mating the conduit connector 23 to the second connector fitting 1120 as described herein. The fin flange 1270 can have any number of shapes and as illustrated, the fin flange 1270 can be a C-shaped structure that mates with the fin 1260. The fin flange 1270 is thus located radially outward from the fin 1260.

Figure 8:
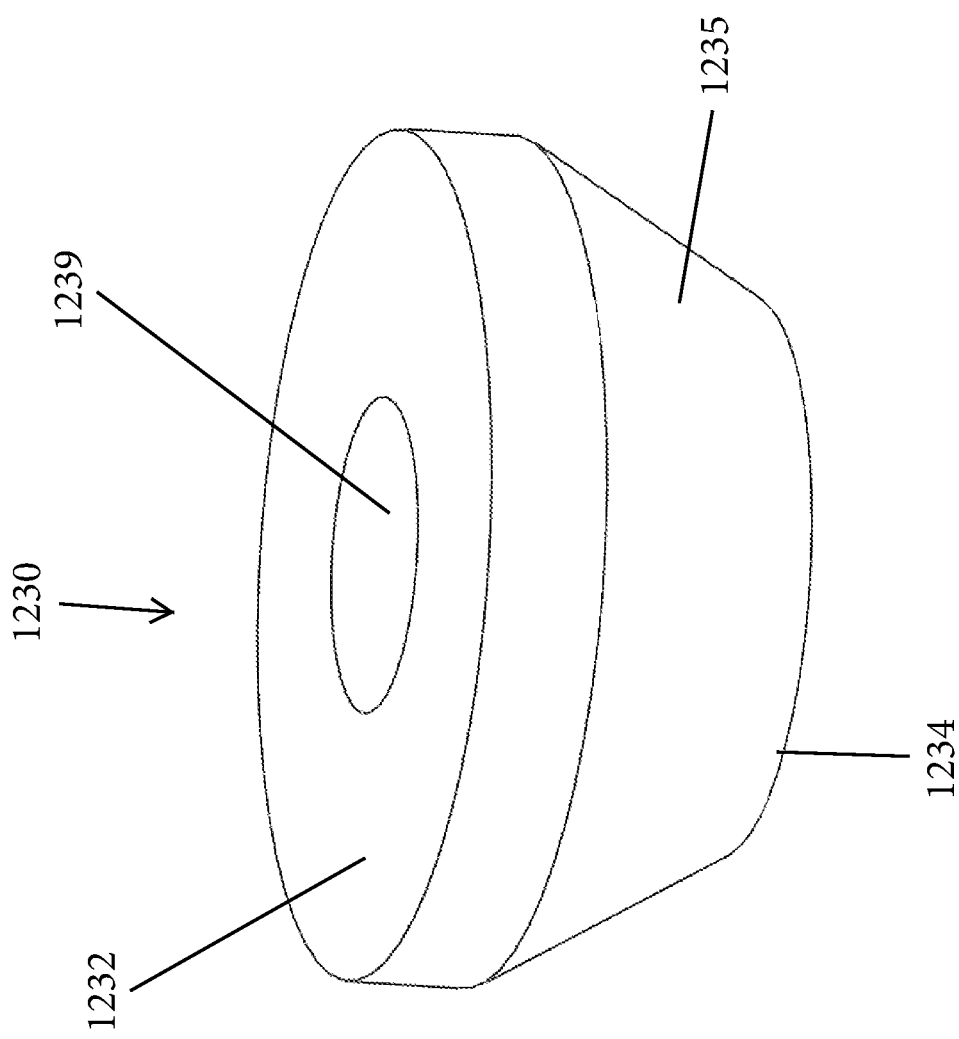
FIG. 8 is a perspective view of a valve seat.

As shown in FIG. 8, the valve seat 1230 is a hollow body that has a first end 1232 and a second end 1234. The body can have a conical shape with the first end 1232 being a proximal surface and the second end 1234 being a distal surface. The first and second ends 1232, 1234 can be planar surfaces that are parallel to one another. A side wall 1235 extend between the ends 1232, 1234. At least a portion of the side wall 1235 can be a beveled edge so as to form the conical shape of the valve seat 1230. The valve seat 1230 has a center bore 1239 that passes therethrough. The center bore 1239 is sized and shaped to receive the cylindrical shaped valve stem 1220 so as to couple the valve seat 1230 to the valve stem 1220. A diameter of the valve seat 1230 is greater at the first end 1232 relative to the second end 1234 (thus, the side wall 1235 tapers inwardly toward the second end 1234).

The valve seat 1230 can be manufactured from any number of different materials, such as a flexible rubber, silicone or an elastomeric material that is designed to seat against the conical seating surface 1225 (FIG. 7B) located on the interior bore of the second fitting 1120.

Figure 9:
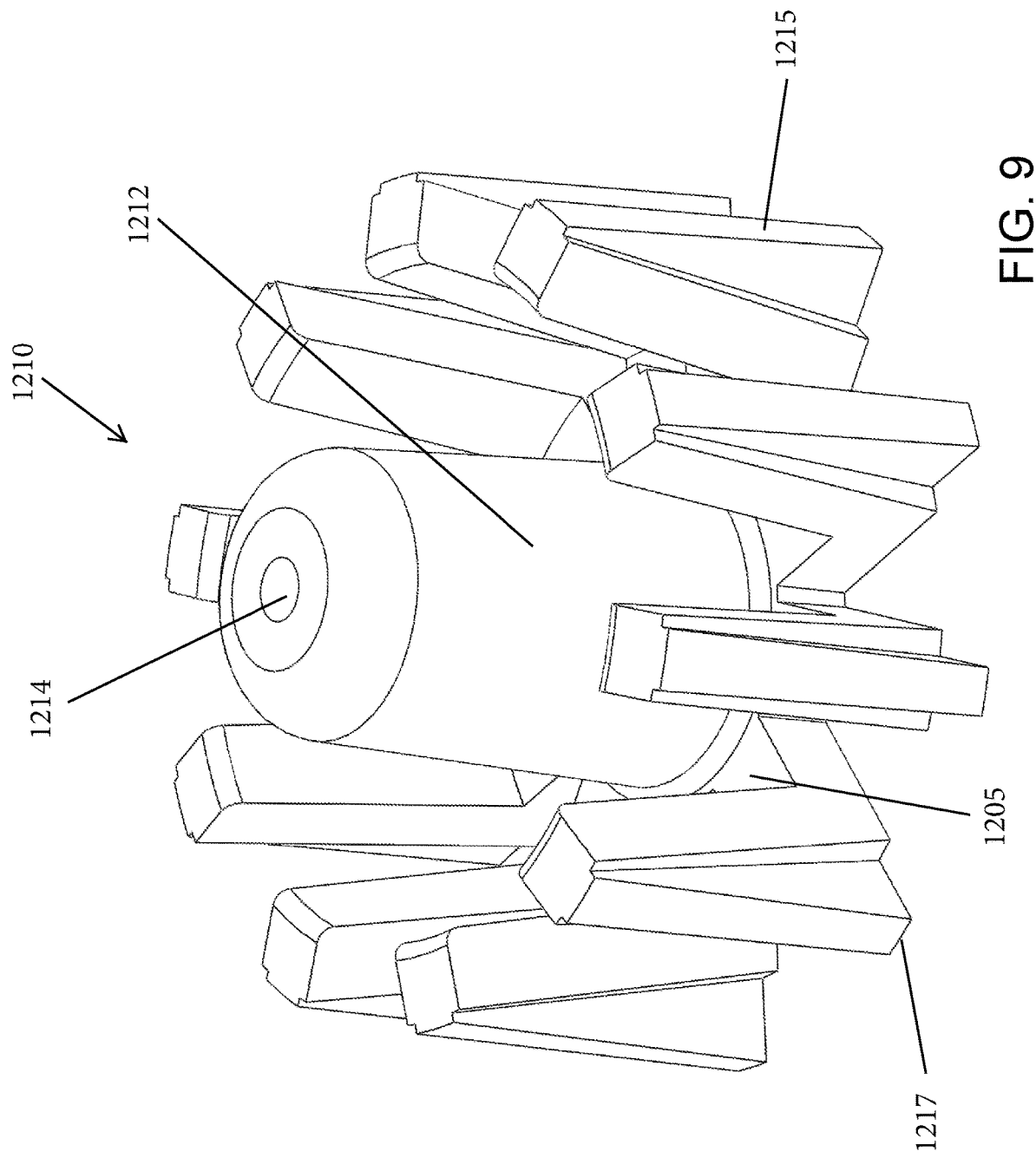
FIG. 9 is a perspective view of a valve poppet.

As shown in FIG. 9, the valve poppet 1210 includes a center hub 1212 and has a center bore 1219 (FIG. 4A) that passes through the center hub 1212 (from a top surface to a bottom surface thereof) and terminates at one end in a vent hole 1214. The center bore 1219 communicates with a thus passes through a center hub 1212. Located circumferentially about the center hub 1212 are a plurality of guide ribs (teeth or fins) 1215. The height of each guide rib 1215 is less than the height of the center hub 1212 resulting in the center hub 1212 extending above the guide ribs 1215. As illustrated, the guide ribs 1215 of the valve poppet 1210 look similar to gear teeth. An underside (distal surface) 1217 of the body of the valve poppet 1210 is a planar surface.

Figure 4A:
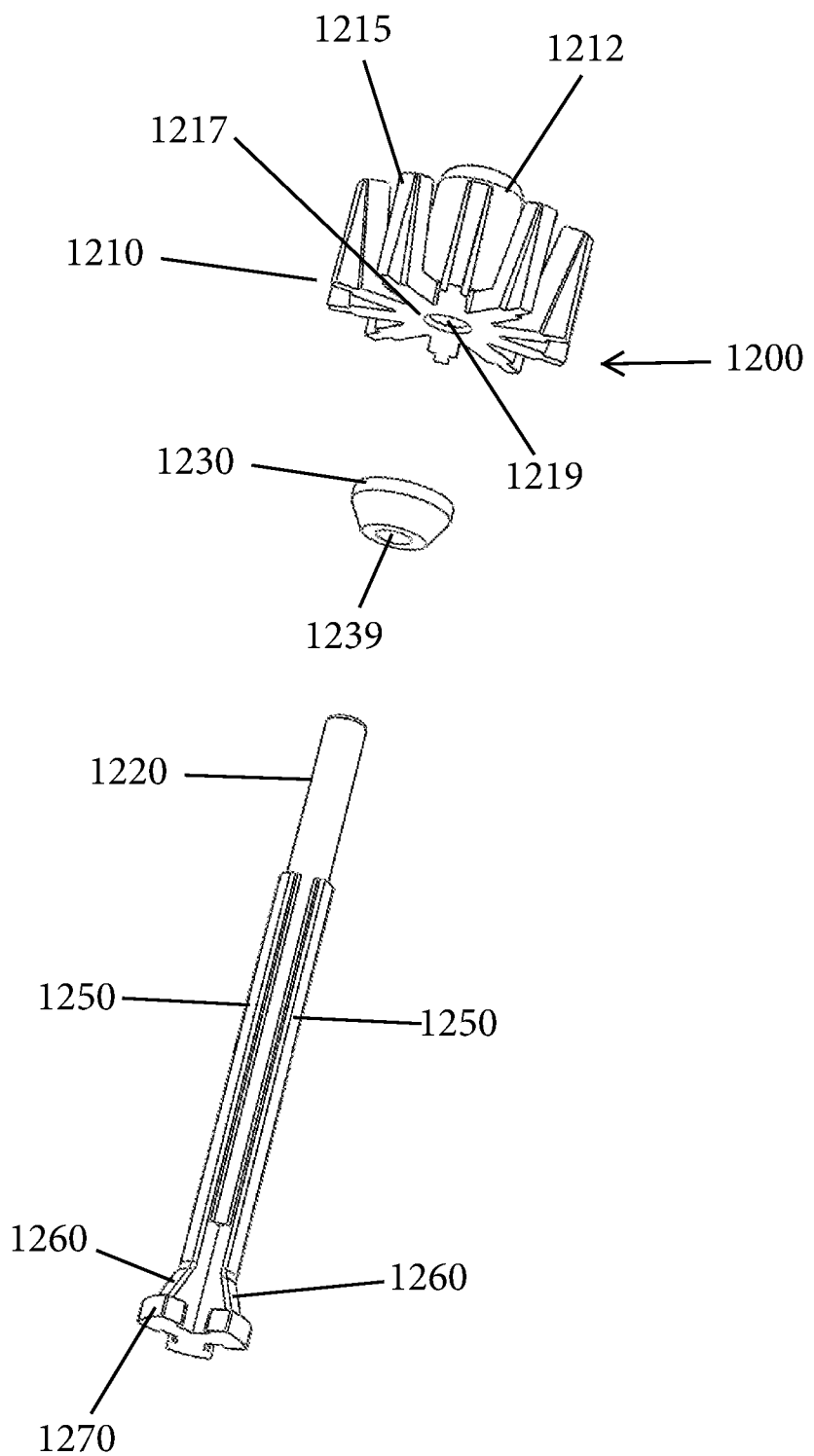
FIG. 4A is an exploded perspective view of a valve assembly.
Figure 4B:
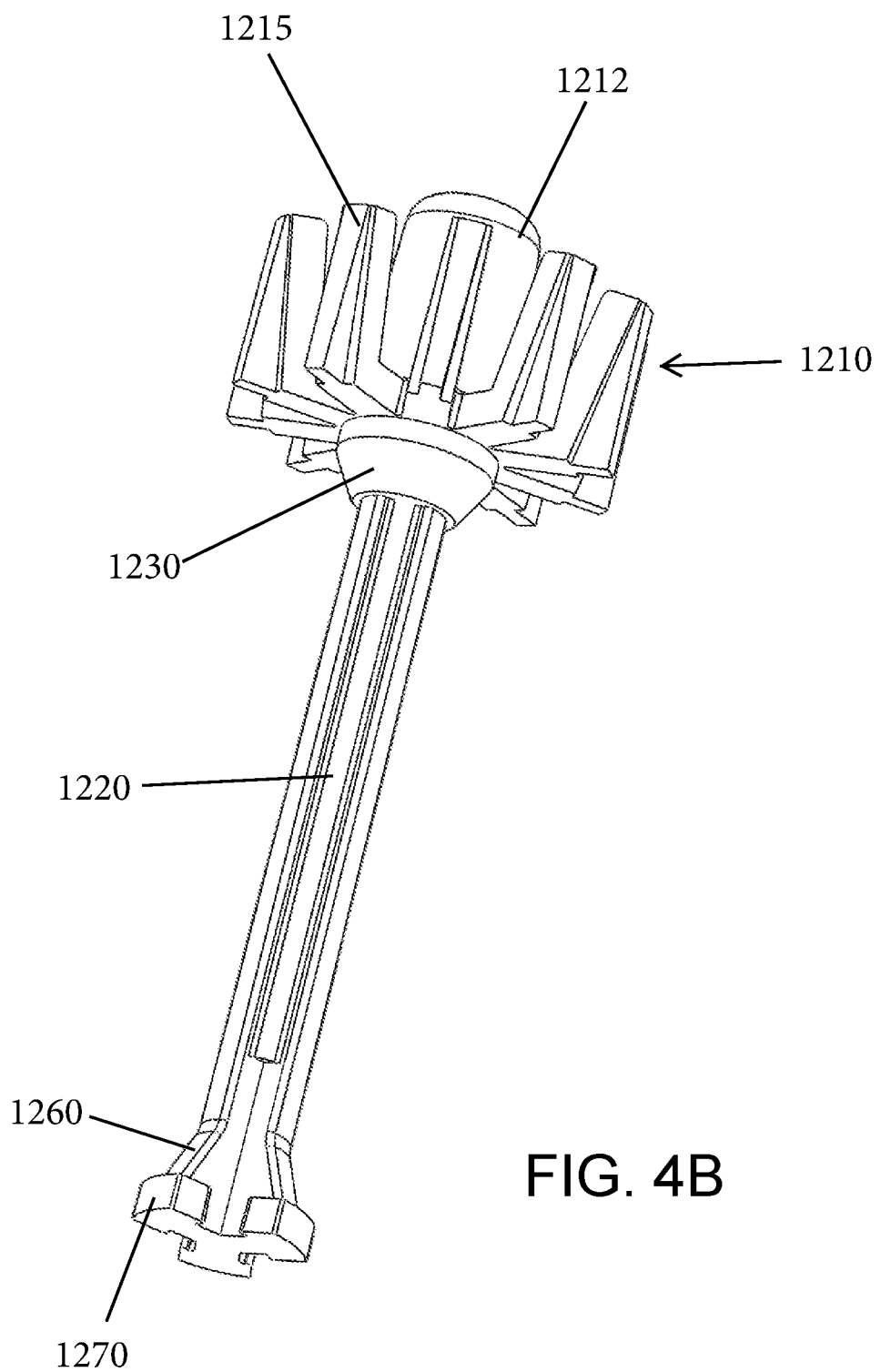
FIG. 4B is a perspective view of the valve assembly in its assembled state.
Figure 5A:
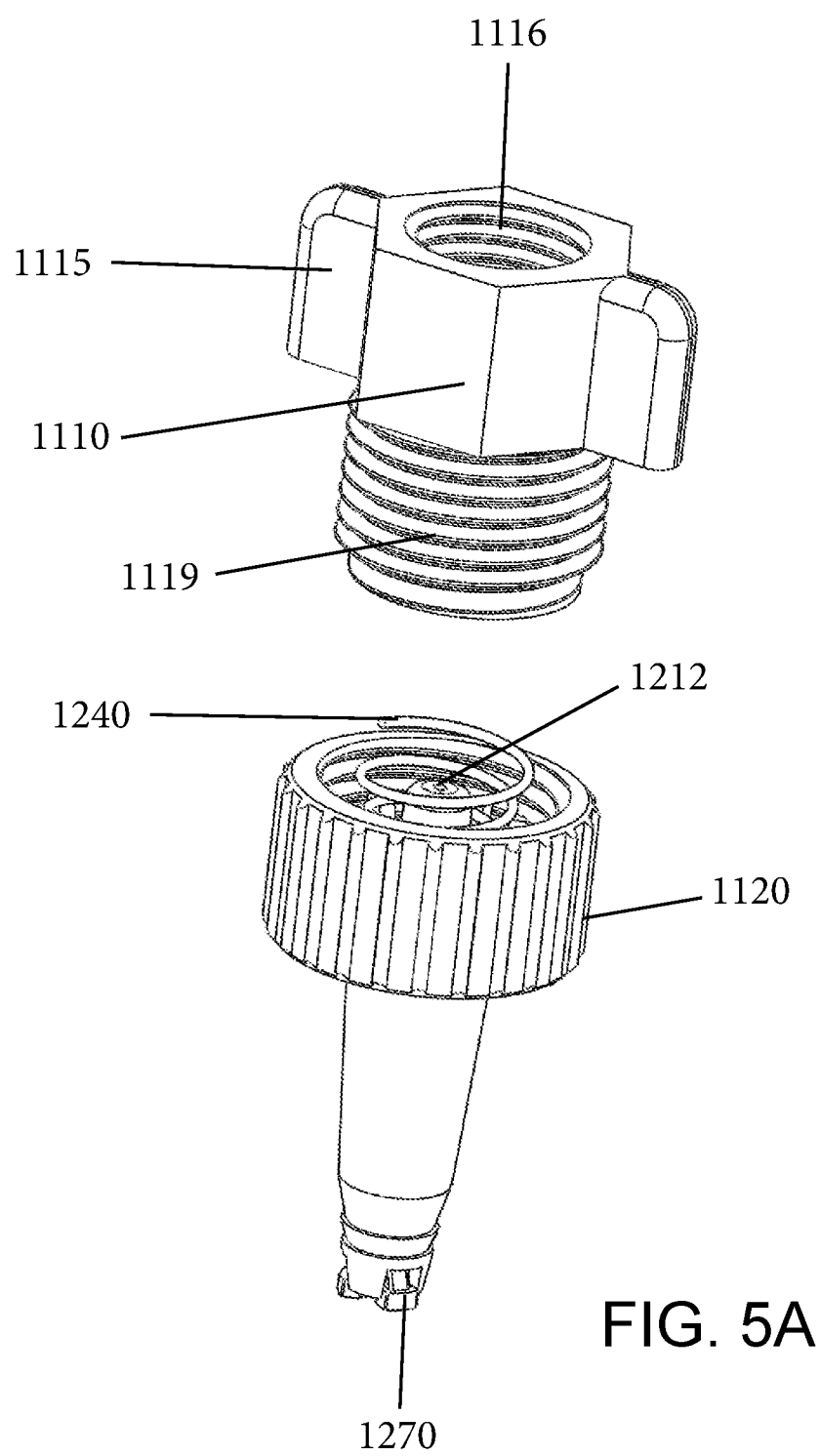
FIG. 5A is an exploded perspective view of first and second parts of the valve assembly.
Figure 5B:
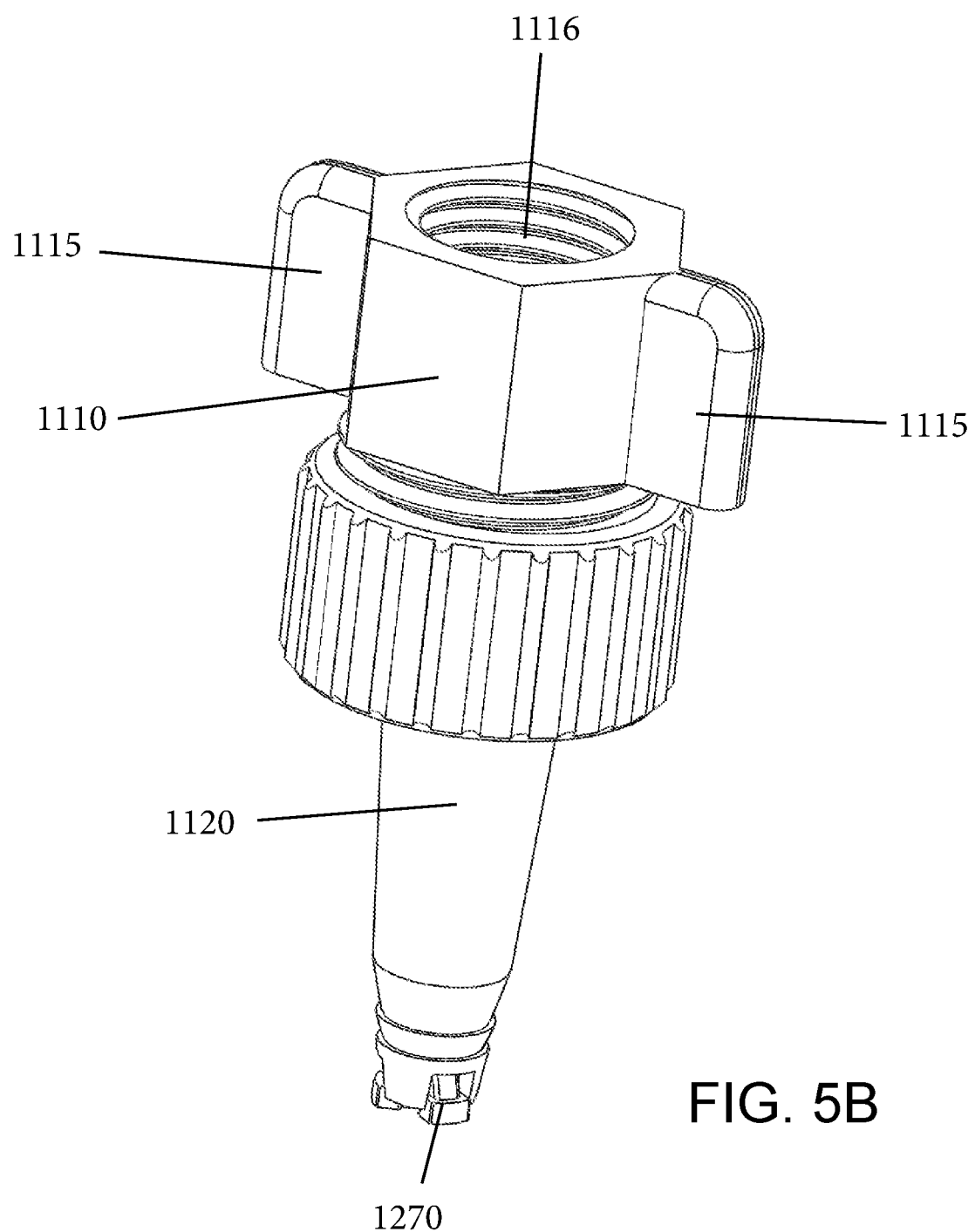
FIG. 5B is a perspective view of the gas concentrator device in its assembled state.

The valve poppet 1210 acts as a piston in a cylinder to guide the motion of the actuator assembly. The guide ribs 1215 of the valve poppet 1210 in conjunction with the first connector fitting 1110, valve stem 1220, and the second connector fitting 1120 axially locate the motion of the actuator during valve operation (See, FIGS. 7A and 7B). The valve poppet 1210 retains the valve stem 1220. When assembled, the valve stem 1220 can be glued, solvent bonded, pressed or threaded into the hub 1212 of the valve poppet 1210 creating the actuator assembly (See, FIGS. 4A and 4B). When the valve is fully assembled, the distal surface 1217 of the valve poppet 1210 is located against the proximal surface of the valve seat 1230 and acts to push the valve seat 1230 against its mating conical seating surface 1225 (FIG. 7B) as a result of compression generated by the spring 1240 (FIGS. 5A and 5B). The annular shaped spring land 1205 (FIG. 9) is the surface of the valve poppet 1210 upon which the spring 1240 exerts force.

The valve poppet 1210 has a spider like geometry which reduces the diametric area of the part and resulting magnitude of force excerpted against the valve seat 1230 by the pressure of the supplied oxygen, typically around 50 psi. The vent hole 1214 located at the proximal end of the retention hub 1212 of the valve poppet 1210 to allow for air to escape during assembly with the valve stem 1220.

Figure 10:
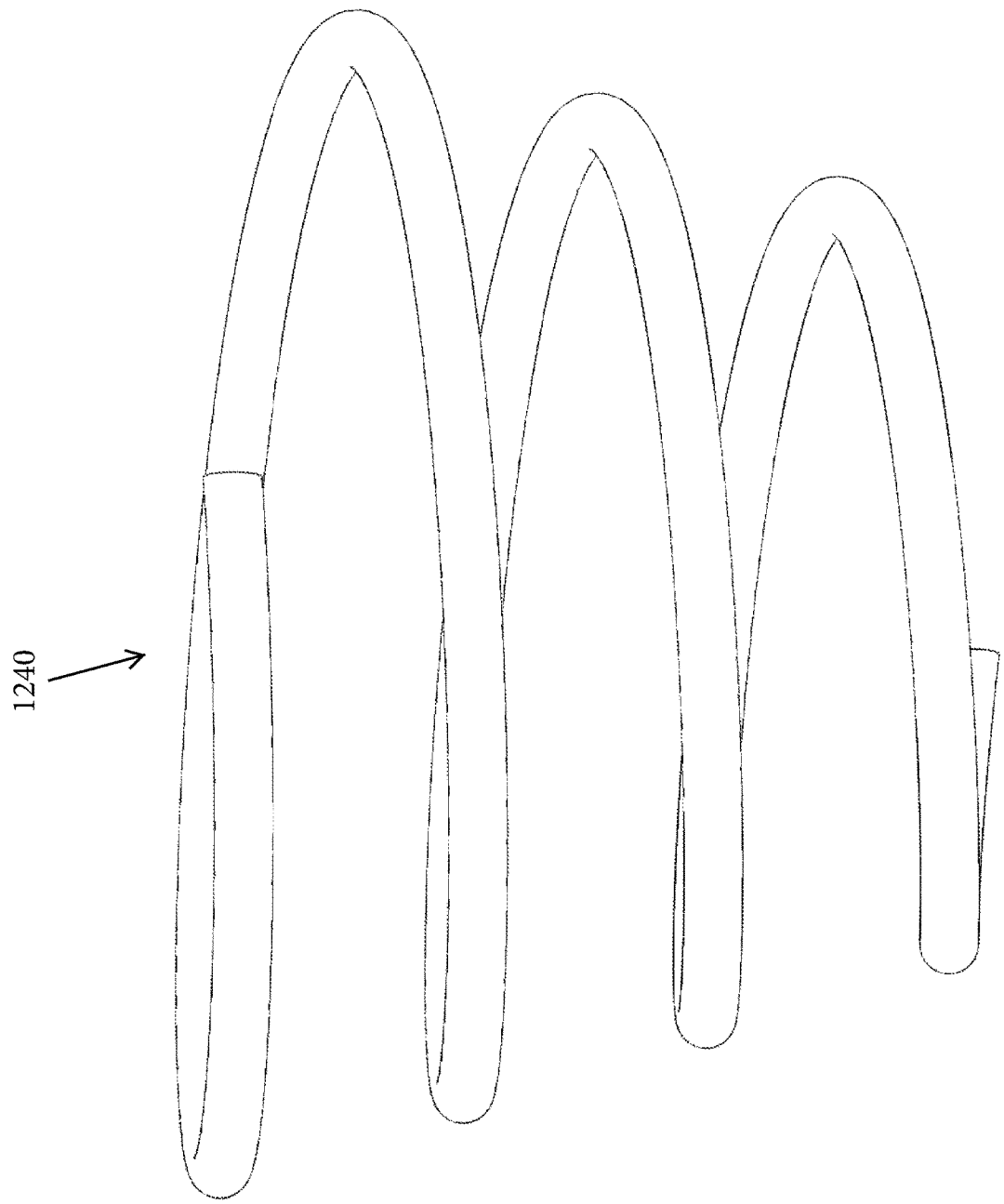
FIG. 10 is a perspective view of a biasing element (e.g., compression spring)

The valve assembly also includes the spring 1240. As shown in FIG. 10, the spring 1240 includes a proximal end 1242 and a distal end 1244 and can be in the form of a compression spring. As shown in the figures, the distal end of the spring 1240 is inserted into the space between the hub 1212 and guide ribs 1215 of the valve poppet 1210. The valve hub 1212 is thus located within the hollow center of the spring 1240 and since both the valve hub 1212 and guide ribs 1215 are upstanding structures, the spring 1240 is maintained in place about the hub 1212. When assembled within the valve, the spring 1240 generates an axial force between the first connector fitting 1110 and the valve poppet 1210. In particular, one end of the spring 1240 seats against the planar underside 1131 (FIG. 11B) of the internal seat 1130 and the other end of the spring 1240 is disposed within the annular shaped spring landing 1205 (FIG. 9) formed in the valve poppet 1210. This force provides leak free valve closure when the valve is not actuated. The spring 1240 is preferably non-magnetic for use around magnetic resonance imaging (MRI) equipment.

The gas connector device 1000 of the present invention provides a number of advantageous features including but not limited to the following: 1) when connected to a gas source 101 and the conduit 20, the valve supplies oxygen or other gas to a patient. Once the conduit 20 is disconnected, gas flow is immediately shut-off (FIG. 7A); 2) the valve is actuated allowing gas flow, via the fins 1260 integral to the valve stem 1220 by simply pushing the standard conduit connector 23 onto the barbed taper of the second fitting 1120; 3) the fin flanges 1270 integral to the valve stem 1220 provide increased surface contact with the inside diameter of the conduit connector 23. This increased surface contact prevents the fins 1260 from penetrating or flexing the inside surface of the (elastomeric) conduit connector 23 allowing the valve to undesirably close (FIGS. 6, 7A and 7B); 4) the taper of the barbed end of the second connector fitting 1120 is specifically designed to control the geometric interaction between the second connector fitting 1120 and the conduit connector 23; 5) the valve poppet 1210 has a spider-like geometry reducing its geometric foot-print and the resulting force against it by the pressure of the incoming gas; and 6) the valve seat 1230 is of conical geometry designed to increase the surface area of seat contact and reduce the overall diameter of the valve seat 1230 and by minimizing the diameter of the valve seat 1230, the resulting force against the valve seat 1230 due to the incoming gas is minimized.

The gas connector device 1000 provides the following benefits: 1) safety—the device 1000 cuts off flow of oxygen due to improper shut-off of oxygen flow from gas source 10 due to haste, negligence and/or both; 2) eliminates fire hazard due to undesired oxygen flow; 3) eliminates the potential for negligence or accidental misuses due to haste in emergency situations (one less thing to worry about for emergency personnel); 4) cost savings due to undesired oxygen or other gas use; 5) time savings for healthcare professionals; 6) cost savings for emergency medical services, hospitals, critical care centers, nursing homes, etc.; and 7) in home safety due to accidental disconnect.

The gas connector devices disclosed herein have widespread use in various different application including but not limited to the following: hospital floors and patient rooms, emergency rooms (ERs), operating rooms (ORs), anesthesiology, oxygen home use, oxygen cylinders, oxygen concentrators, etc. As also mentioned herein, the devices can be used with different gases including but not limited to oxygen, air, nitrous oxide, heliox or any other suitable gas.

The valve assembly 1200 is assembled by positioning the valve seat 1230 below the underside 1217 of the valve poppet 1210 with the first end 1232 of the valve seat 1230 seating against the underside 1217. The center bore 1239 of the valve seat 1230 and the center bore 1219 of the valve poppet 1210 are axially aligned. The first end 1222 of the valve stem 1220 is fed through the center bore 1239 of the valve seat 1230 and into the center bore 1219 of the valve poppet 1210 and the valve stem 1220 is securely attached to the valve poppet 1210 (i.e., within the center bore 1219 of the valve poppet 1210). For example, the valve stem 1220 can be attached to the valve poppet 1210 using any number of suitable techniques, including a solvent or adhesive bond can be formed or the valve stem 1220 can be threaded or press fit into the valve poppet 1210. FIG. 4B shows the valve assembly 1200 in its assembled state.

As described herein, when the valve assembly is disposed within the device, the valve seat 1230 faces the floor defined within the second connector fitting 1120 and the valve poppet 1210 and the spring 1240 are disposed within the hollow interior of the first connector fitting 1110. When the first and second connector fittings 1110, 1120 are threadingly mated to one another, the end 1114 of the first connector fitting 1110 seats against or is disposed proximate to the planar, annular shaped floor or landing 1005 (FIG. 7B) defined within the second connector fitting 1120.

Figure 7A:
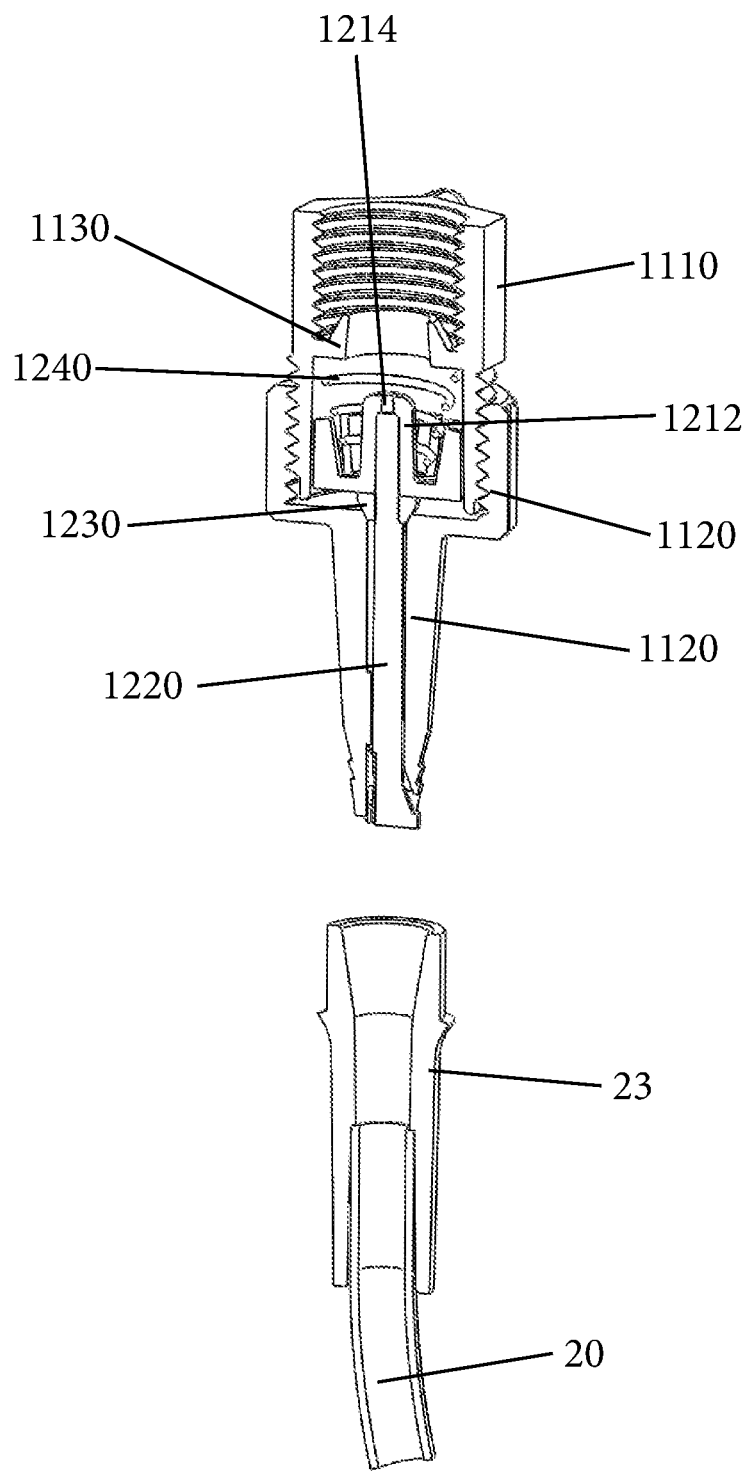
FIG. 7A is a perspective cross-sectional view of the gas concentrator device with a complementary tubing shown in a disconnected state.
Figure 7B:
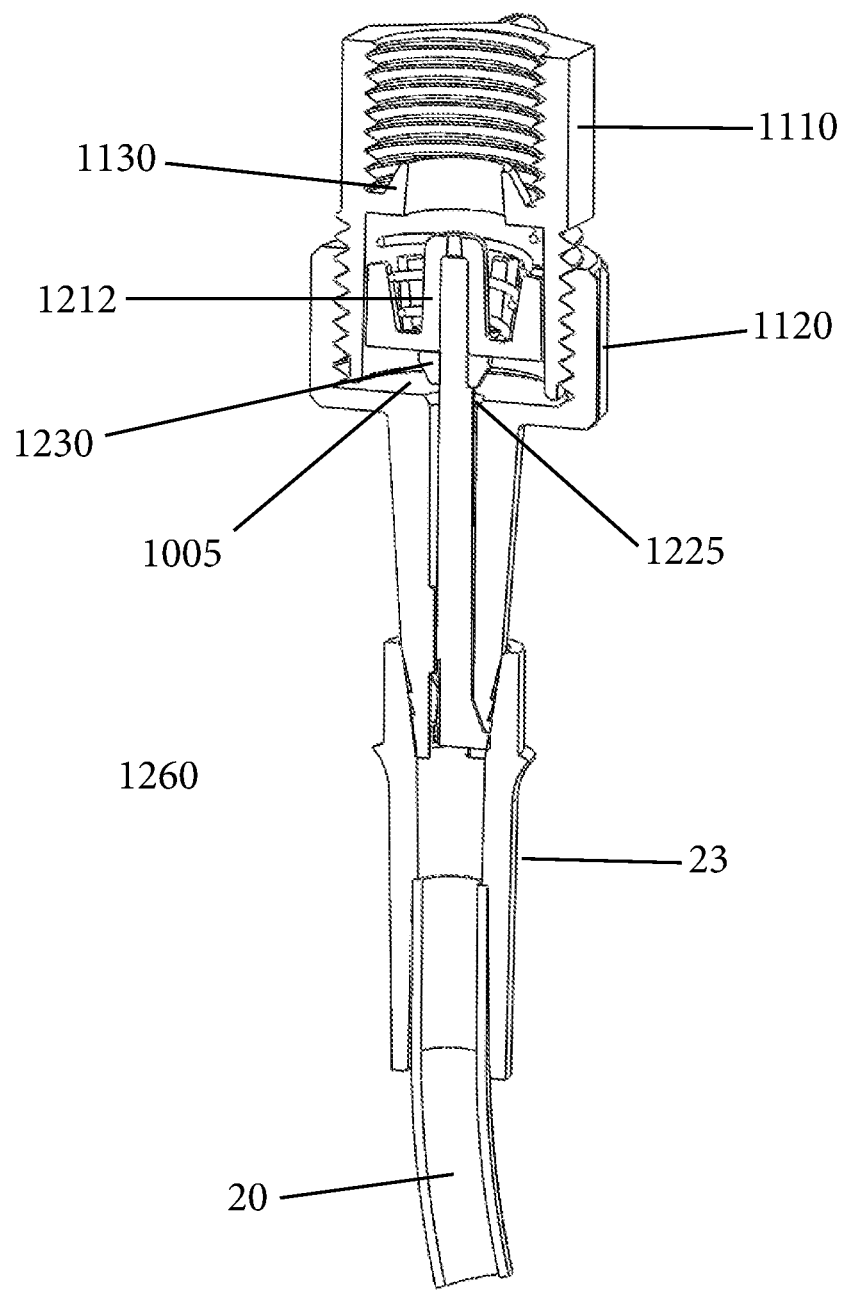
FIG. 7B is a perspective cross-sectional view of the gas concentrator device with the tubing connected thereto.

FIG. 7A shows the valve mechanism in an open position prior to mating the conduit connector 23 of the conduit 20 with the second connector fitting 1120. In this closed position, the valve stem 1220 assumes a distal most position and the fins 1260 and flanges 1270 assume distal most positions within the guide slots 1149. As shown in FIG. 7B, when the conduit connector 23 mates to the second connector fitting 1120 (i.e., the tapered distal portion thereof), the flanges 1270 directly contact the inside diameter of the conduit connector 23 (upon tubing connection and pushed proximally toward the first connector fitting 1110 actuating or opening the valve). In particular, as shown in FIG. 7B, when the valve (mechanism) is opened, the valve seat 1230 is lifted from the conical seating surface 1225 (FIG. 7B) defined within the second connector fitting 1120, thereby fluidly connecting the hollow interior of the first connector fitting 1110 to the hollow interior of the second connector fitting 1120, thereby allowing the gas (e.g., oxygen) to flow from the gas source 101 to the conduit 20. However, once the conduit connector 23 is removed from the barbed tapered distal end portion of the second connector fitting 1120, the spring 1240 applies a distal force to the valve mechanism (i.e., the valve poppet 1210). Since the valve seat 1230 is fixedly attached to the valve poppet 1210, the valve seat 1230 is located below the valve poppet 1210 and prevents the underside of the valve poppet 1210 from seating against a floor formed in the hollow interior of the second connector fitting 1120.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:

1. A gas connector device comprising:
a valve body having an open first end for receiving a gas and an opposing open second end for discharging the gas; and
a valve mechanism that is at least partially contained within the valve body and is configured such that when an axial force is applied thereto, the valve mechanism automatically moves to an open position in which the gas supplied to the open first end is permitted to flow through the valve body to the opposing open second end and when the axial force is removed, the valve mechanism returns to a closed position in which the gas is prevented from flowing through the valve body, wherein the valve mechanism includes an axially movable valve stem that is at least partially contained within the valve body and is biased by a spring such that in an at rest position, the valve mechanism is in the closed position, wherein the valve mechanism includes a valve seat that is disposed about the valve stem and in the closed position, the valve seat seats against a seating surface within the valve body and in the open position, the valve seat is spaced from the seating surface, wherein a distal end of the valve stem includes outwardly projecting flanges that are received within guide slots formed in the valve body at the open opposing second end thereof, the outwardly projecting flanges extending radially beyond an outer surface of the valve body at the opposing open second end thereof so as to lie external to the outer surface of the valve body for being contacted and driven within the guide slots by a conduit connector that is configured for being detachably coupled to the opposing open second end of the valve body by receipt over the opposing second end such that the valve stem and the conduit connector are co-linear when coupled to one another body.

2. The device of claim 1, wherein the valve body comprises a first fitting that includes the open first end and a second fitting that includes the open second end, the first fitting and the second fitting each having a hollow interior and being sealingly coupled to one another.

3. The device of claim 2, wherein the first fitting has inner threads formed at the open first end of the valve body for threadingly mating with the outlet port and outer threads that threadingly mate with inner threads of the second fitting for threadingly coupling the first and second fittings to one another.

4. The device of claim 1, wherein the outwardly projecting flanges extend perpendicular to a longitudinal axis of the valve stem.

5. The device of claim 3, wherein the second fitting has a tapered construction with the guide slots being formed in a distal end thereof which defines the open second end of the device, the second fitting further including locating ribs formed along an inner surface thereof at the distal end and extending longitudinally along the second fitting.

6. The device of claim 5, wherein the guide slots are spaced circumferentially apart from one another at the distal end of the second fitting and the locating ribs are spaced circumferentially apart from one another along the inner surface of the second fitting.

7. The device of claim 2, wherein the first fitting includes an internal conical shaped seat formed along an inner bore of the first fitting, the conical shaped seat being tapered outwardly in a direction toward the second fitting.

8. The device of claim 7, wherein the conical shaped seat has a through hole formed therein and an underside of the conical shaped seat defines an annular shaped surface against which the spring seats.

9. The device of claim 1, wherein the valve mechanism further comprises a valve poppet, the valve seat being disposed along an underside of the valve poppet and seating against an outer shoulder of the valve stem, the seating surface comprising a side wall of a tapered inner bore formed in the second fitting, wherein when the valve mechanism is in the closed position, the valve seat seating against the side wall to close the tapered inner bore.

10. The device of claim 9, wherein the spring applies a biasing force to the valve poppet in a direction toward the open second end to cause the valve stem to be in a fully extended position when no force is applied to the valve stem in a counter direction toward the open first end.

11. The device of claim 9, wherein the valve seat has a conical shape and tapers inwardly in a direction toward the distal end of the valve stem, the valve seat having a center hole through which the proximal end of the valve stem passes and the valve poppet has a center hub with an opening into which the proximal end of the valve stem is fixedly attached.

12. The device of claim 9, wherein the valve poppet includes a plurality of guide ribs that extend circumferentially about the center hub with a first annular shaped space being formed between the center hub and the plurality of guide ribs, the plurality of guide ribs being spaced apart so as to define a plurality of first flow paths therebetween to allow the gas to flow to the open second end.

13. The device of claim 9, wherein a distal end of the valve stem includes a plurality of external longitudinal ribs that are spaced circumferentially about the valve stem, wherein proximal ends of the external longitudinal ribs define the outer shoulder, each external longitudinal rib having a fin extending radially outward at a distal end thereof and one of the outwardly projecting flanges is disposed along one respective fin.

14. The device of claim 13, wherein in the closed position, the valve stem is in a fully extended position and in the open position, the valve stem is in a retracted position, wherein in the fully extended position, the outwardly projecting flanges are spaced further away from end walls of the guide slots than when the valve stem is in the retracted position.

15. The device of claim 14, wherein the spring is disposed within the first annular shaped space with one end of the spring seating against a floor of the first annular shaped space and an opposite end of the spring is in contact with an inner landing formed within a hollow interior of the first fitting.

16. The device of claim 13, wherein the valve poppet includes a plurality of guide ribs that extend circumferentially about a center hub of the valve poppet with a first annular shaped space being formed between the center hub and the plurality of guide ribs, the plurality of guide ribs being spaced apart so as to define a plurality of first flow paths therebetween, wherein between the external longitudinal ribs of the valve stem second flow paths are defined, the first flow path and the second flow paths being in fluid communication with one another to allow the gas to flow through the valve body from the open first end to the open second end.

17. The device of claim 16, wherein the plurality of guide ribs comprise upstanding finger structures that are parallel to the center hub, the valve seat having a planar top surface that seats against the underside of the valve poppet and a planar bottom surface that seats against the outer shoulder, the valve stem being fixedly attached to the valve poppet with the valve seat being carried by the valve stem.

18. A method for automatically controlling the flow of oxygen from a gas source comprising the steps of:
  installing a gas concentrator device on an outlet port associated with the gas source, the gas concentrator device including a valve body and a valve mechanism that is at least partially contained within the valve body and moves between an open position in which the gas is permitted to flow through the valve body and a closed position in which gas is prevented from flowing through the valve body, wherein the valve mechanism includes a biased valve stem that includes outwardly projecting flanges extending radially beyond an outer surface of the valve body at an opposing open second end thereof so as to lie external to the outer surface of the valve body; and automatically providing gas flow from the gas source to a conduit connector that is coupled to a conduit by connecting the conduit connector to the valve body by fitting the conduit connector over the opposing second end of the valve body such that the biased valve stem and the conduit connector are co-linear and urging the outwardly projecting flanges in a direction toward an open first end by moving the conduit connector along the outer surface of the valve body which automatically causes the biased valve stem of the valve mechanism to move axially toward the open first end of the valve body resulting in the opening of the valve mechanism, whereupon removal of the conduit connector from the valve body automatically causes the valve mechanism to assume the closed position.

19. A gas connector system comprising:
  an elongated conduit having a conduit connector at a first end thereof; and
  a gas connector valve device for attachment to the conduit connector, the gas connector valve device comprising:
    a valve body having an open first end for receiving a gas and an opposing second end for discharging the gas; and
    a valve mechanism that is at least partially contained within the valve body and is configured when a force is applied to automatically move between an open position in which the gas is permitted to flow through the valve body and a closed position in which the gas is prevented from flowing through the valve body to the opposing second end, wherein the valve mechanism includes an axially movable valve stem that is at least partially contained within the valve body and is biased by a spring such that in a rest position, the valve mechanism is in the closed position, wherein the valve mechanism includes a valve seat that is disposed about the valve stem and in the closed position, the valve seat seats against a seating surface within the valve body and in the open position, the valve seat is spaced from the seating surface, wherein a distal end of the valve stem includes outwardly projecting flanges that are received within guide slots formed in the valve body at the opposing open second end thereof, the outwardly projecting flanges extending radially beyond an outer surface of the valve body at the opposing open second end thereof so as to lie external to the outer surface of the valve body for being contacted and driven axially within the guide slots by the conduit connector when the conduit connector is detachably coupled to the opposing open second end of the valve body by receipt over the opposing second end such that the valve stem and conduit connector are co-linear when coupled to one another resulting in the valve mechanism automatically moving to the open position due to axial movement of the valve stem in a direction toward the open first end as a result of the outwardly projecting flanges being urged in a direction toward the open first end by the conduit connector.

20. The gas connector system of claim 19, wherein each guide slot has an inner end wall, wherein in the closed position, the valve stem is in a fully extended position and the outwardly projecting flanges are spaced a first distance from the inner end walls and wherein in the open position, the valve stem is in a retracted position and the outwardly projecting flanges are spaced a second distance from the inner end walls, the first distance being greater than the second distance.

21. The gas connector system of claim 19, wherein the conduit connector has a tapered inner diameter section at a first end thereof that receives the open second end of the valve body.

22. The gas connector system of claim 21, wherein an inner diameter of the tapered inner diameter section progressively increases in a direction toward the first end of the elongated conduit, where at the first end of the conduit connector, the outer diameter of the open second end of the valve body is less than the inner diameter of the tapered inner diameter section, while at an inward location, the outer diameter of the open second end of the valve body is greater than the inner diameter of the tapered inner diameter section.

23. The gas connector system of claim 19, wherein the valve mechanism further includes a valve poppet that is coupled to a proximal end of the valve stem, the spring being in direct contact with and applying a biasing force to the valve poppet, the valve seat being disposed about and being carried by the valve stem resulting in the valve poppet, the valve stem and the valve seat moving as one assembly.

24. The gas connector system of claim 23, wherein the valve body comprises a first fitting and a second fitting that threadingly mates with the first fitting, the first fitting defining the open first end of the valve body, the second fitting defining the open second end of the valve body, the first fitting including an inner shoulder against which a first end of the spring seats against, the spring having an opposite second end that seats against the valve poppet.

25. The gas connector system of claim 23, wherein the valve poppet includes a plurality of guide ribs that extend circumferentially about a center hub of the valve poppet with a first annular shaped space being formed between the center hub and the plurality of guide ribs, the spring being received within the first annular shaped space, the plurality of guide ribs being parallel to the center hub, the plurality of guide ribs being spaced apart so as to define a plurality of first flow paths therebetween, wherein the valve stem includes external longitudinal ribs formed along an outer surface of the valve stem and second flow paths being defined between the external longitudinal ribs, the first flow path and the second flow paths being in fluid communication with one another to allow gas to flow through the valve body from the open first end to the open second end.

26. The gas connector system of claim 25, wherein the plurality of guide ribs comprise upstanding finger structures that are parallel to the center hub, the valve seat having a planar top surface that seats against the underside of the valve poppet and a planar bottom surface that seats against the outer shoulder.

\* \* \* \* \*